United States Patent [19]
VanWagenen et al.

[11] Patent Number: 5,648,541
[45] Date of Patent: Jul. 15, 1997

[54] CHIRAL REDUCTIONS OF IMINES LEADING TO THE SYNTHESES OF OPTICALLY ACTIVE AMINES

[75] Inventors: Bradford C. VanWagenen; Robert M. Barmore, both of Salt Lake City, Utah

[73] Assignee: NPS Pharmaceuticals, Inc., Salt Lake City, Utah

[21] Appl. No.: 535,469

[22] Filed: Sep. 28, 1995

[51] Int. Cl.$^6$ .................................................. C07C 209/52
[52] U.S. Cl. ........................... 564/375; 564/374; 564/378
[58] Field of Search ................................. 564/375, 374, 564/378

[56] References Cited

U.S. PATENT DOCUMENTS

| | | | |
|---|---|---|---|
| 2,798,094 | 7/1957 | Shepard et al. | 564/374 |
| 4,024,274 | 5/1977 | Druckrey et al. | 514/466 |
| 4,925,664 | 5/1990 | Jackson et al. | 424/537 |
| 5,064,657 | 11/1991 | Jackson et al. | 424/537 |
| 5,300,437 | 4/1994 | Stirling et al. | 435/280 |
| 5,326,784 | 7/1994 | Junien et al. | 514/456 |
| 5,504,253 | 4/1996 | VanWagenen et al. | 564/374 |

FOREIGN PATENT DOCUMENTS

| | | |
|---|---|---|
| 58-41847A2 | 3/1983 | Japan . |
| 0069058 | 4/1985 | Japan . |
| 404018058A | 1/1992 | Japan . |
| 406001757A | 1/1994 | Japan . |
| WO93/04373 | 3/1993 | WIPO . |

OTHER PUBLICATIONS

"ASN Program & Abstracts", *Journ. Am. Soc. Neph.*, vol. 4, No. 3, 120P, 69P, pp. 719, Sep., 1993.

Barnes et al., "The Use of 4-Substituted Hydrindenes in the Preparation of Cyclopentanophenanthrene Derivatives", *Journ. Am. Chem. Soc.*, vol. 71, pp. 2644–2647, Aug., 1949.

Barney et al., "A Convenient Synthesis Of Hindered Amines And α-Trifluoromethylamines From Ketones", *Tetrahedron Letters*, vol. 31, No. 39, pp. 5547–5550, 1990.

Brussee et al., "Synthesis Of Optically Active Ethanolamines", *Tetrahedron*, 46(5):1653–1658, 1990.

Chemical Abstracts, 99:104949b, 1983, vol. 99, pp. 558.

Chemical Abstracts, 116:128255t, 1992, vol. 116, pp. 823.

Cho et al., "A Direct Comparison Study of Asymmetric Borane Reduction of C=N Double Bond Mediated by Chiral Oxazaborolidines", *Bull. Korean Chem. Soc.*, vol. 15, No. 1, pp. 53–57, 1994.

1993 Program & Abstracts, *Journal of Bone and Mineral Research*, vol. 8, Supplement 1, pp. S175, S181, Aug. 1993.

Jasys et al., "The Total Synthesis Of Argiotoxins 636, 659 And 673", *Tetrahedron Letters*, vol. 29, No. 48, pp. 6223–6226, 1988.

Kang et al., "Rhodium (*I*)—catalysed Asymmetric Hydrogenation of Imines", *J. Chem. Soc. Commun.*, pp. 1466–1467, 1988.

Marino et al., "An Improved Synthesis Of 3-Methyl-5-Hydroxy Protected Indoles", *Synthetic Communications*, 24(6):839–848, Mar., 1994.

Mattson et al., "an Improved Method for Reductive Alkylation of Amines Using Titanium (IV) Isopropoxide and Sodium Cyanoborohydride", *J. Org. Chem.*, vol. 55, No. 8, pp. 2552–2554, 1990.

Nason et al., "Synthesis of Neurotoxic Nephila Spider Venoms: NSTX–3 and JSTX–3", *Tetrahedron Letters*, vol. 30, No. 18, pp. 2337–2340, 1989.

Sheldon, Roger A., "The Industrial Synthesis Of Pure Enantiomers", *Drug Information Journal*, vol. 24, pp. 129–139, 1990.

Takayanagi et al., "Total Synthesis of Sarcophytol A, an Anticarcinogenic Marine Cembranoid", *J. Org. Chem.*, vol. 59, pp. 2700–2706, 1994.

Terashima et al., "Asymmetric Reduction Of Simple Archiral Ketones With Lithium Aluminum Hydride Partially Decomposed By (–)-N–Methylephedrine and N–Ethylaniline", *The Chemical Society of Japan*, Chemistry Letters, pp. 981–984, 1980.

Viso et al., "Kinetic Resolution of Racemic Disubstituted 1-Pyrrolines via Asymmetric Reduction with a Chiral Titanocene Catalyst", *J. Am. Chem. Soc.*, vol. 116, No. 20, pp. 9373–9374, 1994.

Willoughby et al., "Catalytic Asymmetric Hydrognation of Imines with a Chiral Titanocene Catalyst: Scope and Limitations", *J. Am. Chem. Soc.*, vol. 116, No. 20, pp. 8952–8965, 1994.

(List continued on next page.)

*Primary Examiner*—Richard L. Raymond
*Attorney, Agent, or Firm*—Trask, Britt & Rossa

[57] ABSTRACT

A process for preparing an R enantiomer of a compound of the formula (I):

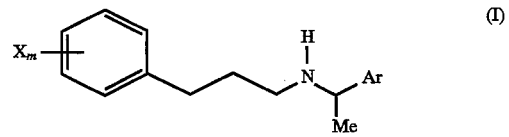

wherein Ar is 3-methoxyphenyl, 3-chlorophenyl, or 1-naphthyl, and X is independently selected from the group consisting of H, F, Cl, Br, I, phenyl, $CF_3$, $CF_2H$, $CFH_2$, lower alkyl (e.g., Me), O-lower alkyl (e.g., OMe), $OCH_2CF_3$, OH, CN, $NO_2$, C(O)-lower alkyl (e.g., C(O)Me), C(O)O-lower alkyl (e.g., C(O)OMe), C(O)NH-lower alkyl (e.g., C(O)NH—Me), C(O)N-lower alkyl$_2$ (e.g., C(O)NMe$_2$), OC(O)-lower alkyl (e.g., OC(O)Me), and NH—C(O)-lower alkyl (e.g., NH—C(O)Me), where "lower alkyl" is selected from a group consisting of 1 to 6 carbon atoms, and m is an integer between 1 and 5, by asymmetrically and enantioselectively reducing an imine with a reducing agent/chiral auxiliary agent complex so as to produce an enantiomeric excess of R enantiomer of the compound of formula (I) over the S enantiomer of the compound of formula (I). The process is especially useful to produce compounds (R)-(+)-N-[1-(3-methoxyphenyl)ethyl]-3-(2-chlorophenyl)propanamine and (R)-(+)-N-[1-(3-methoxyphenyl)ethyl]-3-(phenyl)propanamine. Enantiomeric excess of the R enantiomer over S enantiomer of greater than 65% have been achieved.

20 Claims, 2 Drawing Sheets

OTHER PUBLICATIONS

Yamada et al., "Asymmetric Reduction of Cyclic Imines with Chiral Sodium Acyloxyborogyrides", *J. Chem. Soc.*, Perkin Trans. I, pp. 265–270, 1983.

Zandbergen et al., "A One-Pot Reduction-Transamination-Reduction Synthesis of N-substituted β-Ethanoloamines from Cyanohydrins", *Tetrahedron*, 48(19):3977–3982, 1991.

Zhu et al., "Asymmetric Reductions Of Carbon-Nitrogen Double Bonds. A Review", *Organic Preparations And Procedures Int.*, 26(2), pp. 193–236, 1994.

CHIRAL REDUCTIONS OF IMINES LEADING TO THE SYNTHESES OF OPTICALLY ACTIVE AMINES

BACKGROUND OF THE INVENTION

1. Technical Field

The invention relates to methods for reducing an imine to an amine, and more specifically to the enantioselective reduction of an imine using a chiral reducing agent to generate a chiral amine product of enhanced enantiomeric excess.

2. Background Art

As disclosed in Fox et al., "A First Generation Calcimimetic Compound (NPS R-568) that Acts on the Parathyroid Cell Calcium Receptor: A Novel Therapeutic Approach for Hyperparathyroidism," *Journal of Bone and Mineral Research*, 8: S181, Abstract 260 (Suppl. 1, Aug., 1993), compounds such as (R)-(+)-N-[1-(3-methoxyphenyl)ethyl]-3-(2-chlorophenyl)propanamine (chem. abstr. index name, also known as, e.g., (R)-(+)-N-[3-(2-chlorophenyl)propyl]-α-methyl-3-methoxybenzylamine or (R)-(+)-N-[3-(2-chlorophenyl)propyl]-1-(3-methoxyphenyl)ethylamine), i.e.:

have utility in the treatment of hyperparathyroidism and possibly other bone and mineral-related disorders and diseases such as osteoporosis.

As disclosed in Zhu et al. "Asymmetric Reductions of Carbon-Nitrogen Double Bonds. A Review", *Organic Preparation and Procedures International.*, 26 (2)193–236 (1994): "Reagents prepared from reaction of LiAlH$_4$ with (−)-menthol or (+)-borneol were used to reduce several aliphatic imines to the corresponding mines, but the enantiomeric excesses obtained were low (i.e., 1.8–9.9% ee). Also, the use of optically active α-phenylethylamine-borane complex for the reductive amination of prochiral ketones to produce chiral amines has also been investigated, but gave very low enantioselectivities (1.1–1.6% ee)."

Although the successful chiral reduction of ketones to alcohols has been thoroughly documented in the literature, the reductions of imines to chiral amines, as indicated above (from Zhu et at.), has given, at best, poor yields (<10% ee). A straightforward chemical synthesis yielding (R)-(+)-N-[3-(2-chlorophenyl)propyl]-1-(3-methoxyphenyl)ethylamine, and similar analogs (in greater than 10% ee), using readily available inexpensive, and achiral starting materials would be an improvement in the art.

DISCLOSURE OF THE INVENTION

The invention includes a process for preparing the R enantiomers of compounds of the general formula (I):

where Ar is 3-methoxyphenyl, 3-chlorophenyl, or 1-naphthyl, and X is independently selected from the group consisting of H, F, Cl, Br, I, phenyl, CF$_3$, CF$_2$H, CFH$_2$, lower alkyl (e.g., methyl or "Me"), O-lower alkyl (e.g., OMe), OCH$_2$CF$_3$, OH, CN, NO$_2$, C(O)-lower alkyl (e.g., C(O)Me), C(O)O-lower alkyl (e.g., C(O)OMe), C(O)NH-lower alkyl (e.g., C(O)NH—Me), C(O)N-lower alkyl$_2$ (e.g., C(O)NMe$_2$), OC(O)-lower alkyl (e.g., OC(O)Me), and NH—C(O)-lower alkyl (e.g., NH—C(O)Me), where "lower alkyl" is preferably a saturated branched or unbranched hydrocarbon having one to six carbon atoms, e.g. methyl, ethyl ("Et"), or isopentyl, and where m is an integer between 1 and 5.

These compounds are produced by the enantiomeric reduction of an imine of the formula (II):

with a chiral reducing agent so as to produce an enantiomeric excess (% ee) of the R enantiomer of the compound of formula (I) over the S enantiomer of the compound of the formula (I).

The preferred compounds produced by this process are as follows:

The process is especially useful to produce the most preferred compounds (R)-(+)-N-(3-phenylpropyl)-1-(3-methoxyphenyl)ethylamine and (R)-(+)-N-[3-(2-chlorophenyl)propyl]-1-(3-methoxyphenyl)ethylamine:

In one such process, the imine III is formed by the condensation of 3-phenyl-1-propylamine with 3'-methoxyacetophenone. The intermediate imine III is then reduced with a chiral reducing agent to yield the product IV ((R)-(+)-N-(3-phenylpropyl)-1-(3-methoxyphenyl)ethylamine), with an enantiomeric excess greater than 10%.

The same process is used to prepare (R)-(+)-N-[3-(2-chlorophenyl)propyl]-1-(3-methoxyphenyl)ethylamine. Condensation of 3(2-chloro)phenyl-1-propylamine with 3'-methoxyacetophenone generates the imine V which is then reduced with a chiral reducing agent to yield (R)-(+)-N-[3-(2-chlorophenyl)propyl]-1-(3-methoxyphenyl)ethylamine, with an enantiomeric excess greater than 10%.

BEST MODE OF THE INVENTION

Figure 1:
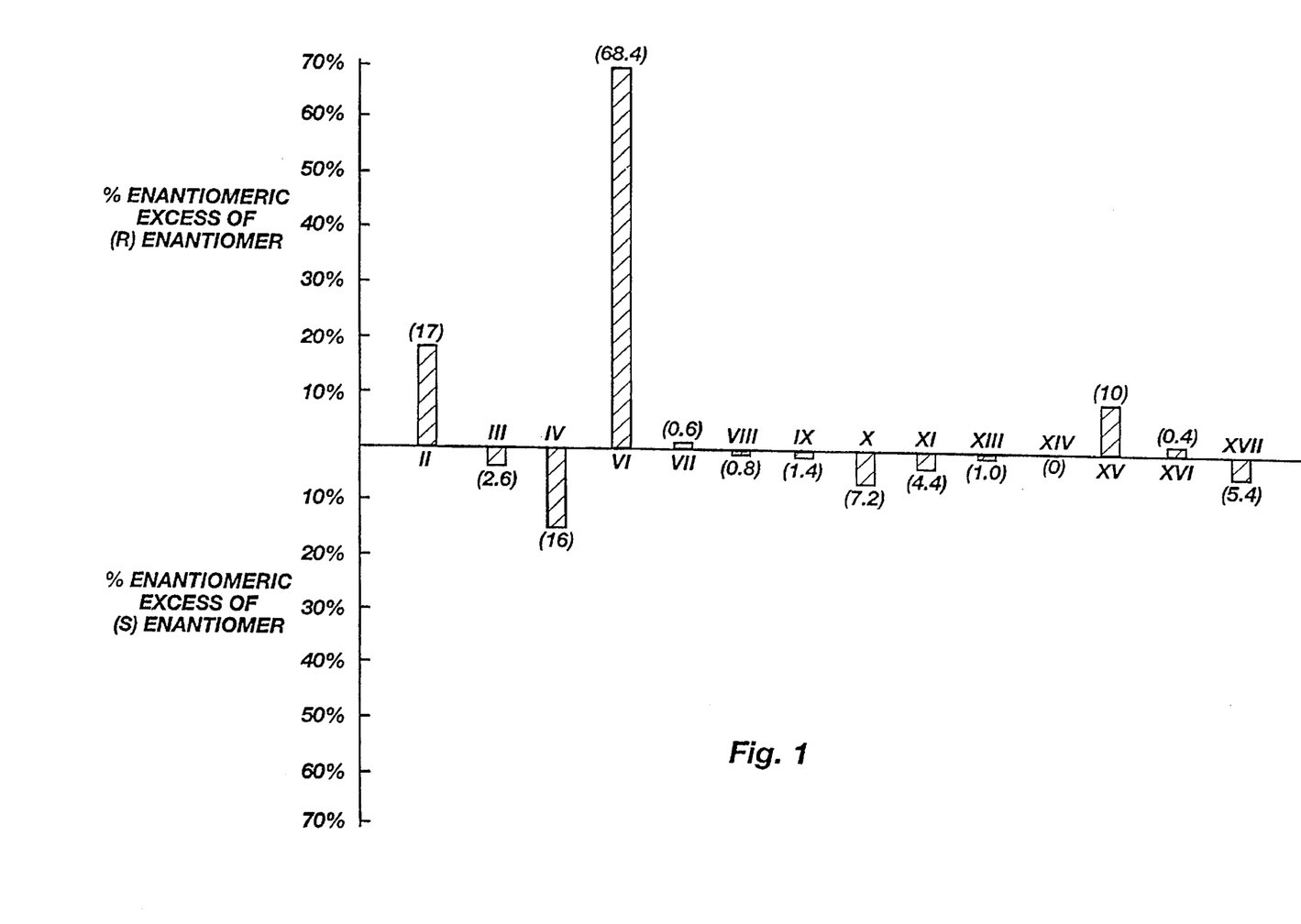
FIG. 1 is a bar graph depicting the results of Tables A and B.
Figure 2:
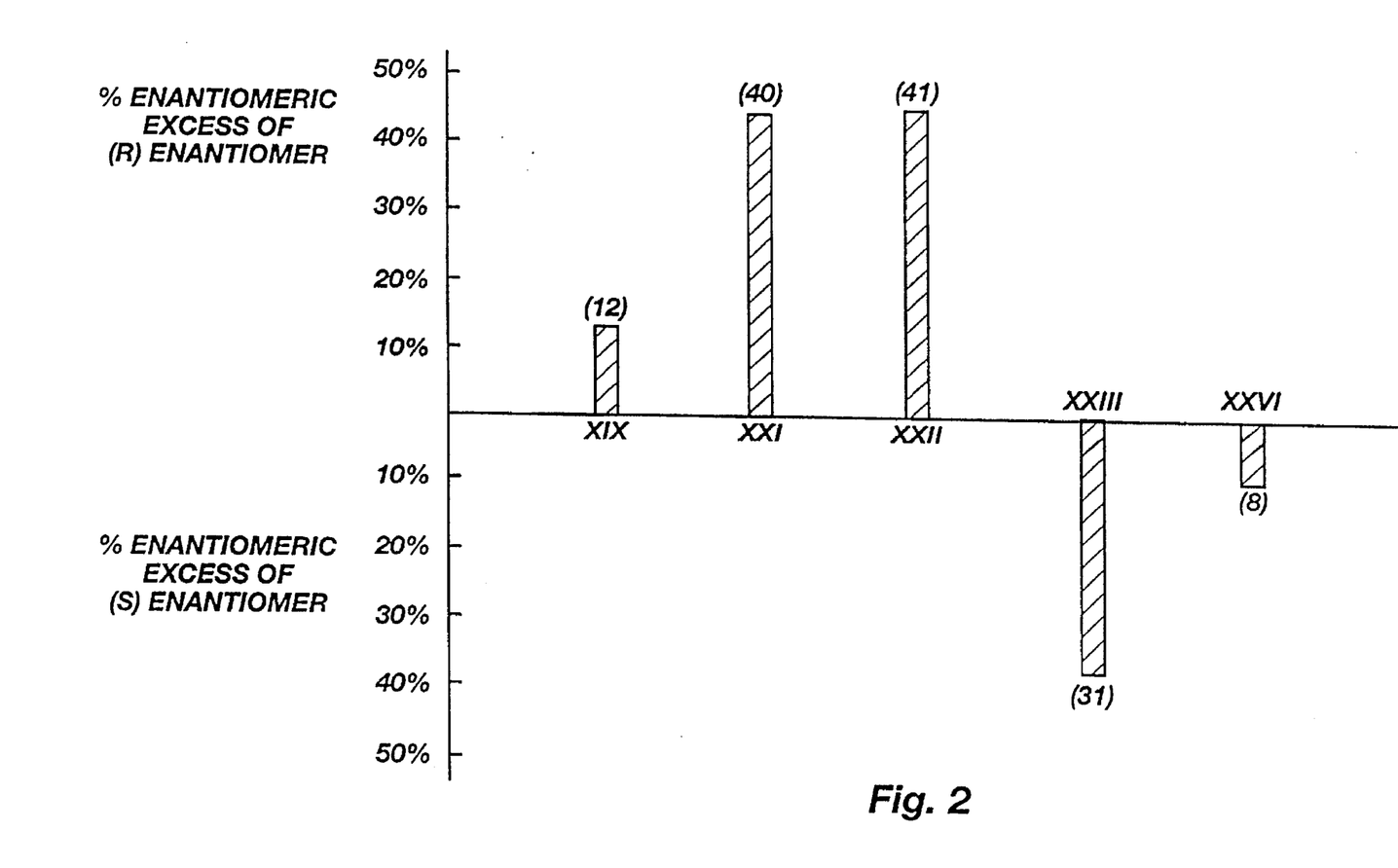
FIG. 2 is a bar graph depicting the results of Table C.

The preferred reducing agents for use in the process include lithium aluminum hydride or borane in combination with a chiral auxiliary selected from the group consisting of (S)-(+)-2-(anilinomethyl)pyrrolidine, (S)-(–)-nicotine, (S)-(–)-1,1'-bi-2-naphthol, (1R,2S)-(–)-ephedrine, (1R,2S),-(–)-

N-methylephedrine, (S)-(+)-1-(2-pyrrolidinylmethyl) pyrrolidine, (S)-(−)-1-methyl-2-pyrrolidinemethanol, (R)-(+)-α,α-diphenyl-2-pyrrolidinemethanol, (R)-(+)-1,1'-bi-2-naphthol, (1R,2S)-(−)-N-methylpseudoephedrine, (2S,3R)-(+) 4 dimethylamino-1,2-diphenyl-3-methyl-2-butanol, and (S)-(−)-α,α-diphenyl-2-pyrrolidinemethanol.

When the reducing agent is lithium aluminum hydride, the preferred chiral auxiliaries are (S)-(+)-2-(anilinomethyl) pyrrolidine, (1R,2S)-(−)-ephedrine, (1R,2S),-(−)-N-methylephedrine, and (R)-(+)-1.1'-bi-2-naphthol.

When the reducing agent is borane, the preferred chiral auxiliary is (S)-(+)-1-(2-pyrrolidinylmethyl)pyrrolidine.

The invention is further explained by reference to the following illustrative EXAMPLES.

EXAMPLES

The following abbreviations have been assigned to the solvents or reagents used:

IPA=isopropanol
DEA=diethylamine
THF=tetrahydrofuran
Et$_2$O=diethyl ether

Example I

Preparation of 1-methyl-1-(3-methoxy)phenyl-5-phenyl-2-aza-1-pentene (Imine III)

A 500 ml round-bottomed flask containing about 22.5 g (167 mmol) of 3-phenyl-1-propylamine (Aldrich Chemical Co., Milwaukee, Wis., U.S.A.) and about 20.2 g (167 mmol) of 3'-methoxyacetophenone (Aldrich Chemical Co., Milwaukee, Wis., U.S.A.) was heated at about 150° C. with stirring, under vacuum (water aspirator) for about 3 hours. The reaction was then heated at about 100° C. under vacuum 10 (microns) for about 15 minutes. This process afforded 1-methyl-1-(3-methoxy)phenyl-5-phenyl-2-aza-1-pentene (imine III), a single component, as analyzed by GC/EI-MS: m/z (rel. int.) 267 (M$^+$, 5), 252 (1), 276 (5), 162 (100), 148 (8), 132 (14), 121 (15), 104 (4), 91 (38), 77 (100).

Example II

Reduction of Imine III with (S)-(+)-2-(anilinomethyl)pyrrolidine/LiAlH$_4$ Complex A solution of (S)-(+)-2-(anilinomethyl)pyrrolidine (about 250 mg. [1.4 mmol]) in diethyl ether (about 5 ml) was added to a stirred solution of LiAlH$_4$ (about 54.6 mg [1.4 mmol]) in diethyl ether (about 5 ml). The reaction was stirred for about 2 hours at room temperature (about 23° C.) and treated with a solution of the imine III (about 300 mg [1.1 mmol]) in diethyl ether (about 3 ml). The reaction was stirred for about 60 hours and quenched by the addition of saturated NH$_4$Cl. The resulting mixture was basified by the addition of a sufficient amount 10N NaOH to raise the mixture above a pH of about 12 and extracted with diethyl ether. GC/EI-MS analysis of this solution showed complete reduction of the imine III to yield (R)-(+)-N-(3-phenylpropyl)-1-(3-methoxyphenyl)ethylamine (100%). The ether extract was concentrated to an oil and a portion of this material chromatographed on a silica gel plate using 5% methanol in chloroform. The product was collected from the plate (R$_f$ 0.75) and subjected to chiral HPLC (High Pressure Liquid Chromatography) analysis. Chromatography through CHIRALCEL OD (0.46×25 cm) using 0.6% IPA in hexane containing 0.1% DEA at 1 ml/min. measuring optical density at 260 mm, showed an enantiomeric excess (R) enantiomer) of 17%. The results are reported in Table A.

Example III

Reduction of Imine III with (S)-(−)-nicotine/LiAlH$_4$

A suspension of LiAlH$_4$ (about 39 mg [1 mmol]) in diethyl ether (about 10 ml) was cooled to about −78° C. and treated, dropwise, with a solution of (S)-(−)-nicotine (about 162 mg [1 mmol]) in diethyl ether. The reaction was stirred at room temperature for about 4 hours, cooled to about −78° C., and treated with a solution of the imine III (about 267 mg [1 mmol]) in diethyl ether (about 1 ml). The reaction was allowed to warm slowly to room temperature where it was stirred for about 72 hours. The reaction was quenched with a sufficient amount of 6N HCl, then basified to a pH above about 12 with 10N NaOH, and extracted with diethyl ether. GC/EI-MS analysis showed a 78% yield of (R)-(+)-N-(3-phenylpropyl)-1-(3-methoxyphenyl) ethylamine. Preparative TLC (thin layer chromatography) and chiral HPLC analysis (as in Example II) showed an enantiomeric excess (S enantiomer) of 3%. The results are reported in Table A.

Example IV

Reduction of Imine III with (S)-(−)-1,1'-bi-2-naphthol/LiAlH$_4$

Reduction of imine III was performed in a manner similar to that of Example III using (S)-(−)-1,1'-Bi-2-naphthol as the chiral auxiliary. GC/EI-MS analysis showed a 24% yield of (R)-(+)-N-(3-phenylpropyl)-1-(3-methoxyphenyl) ethylamine. Preparative TLC and chiral HPLC analysis (as in Example II) showed an enantiomeric excess (S enantiomer) of 16%. The results are reported in Table A.

Example V

Reduction of Imine III with (1R,2S)-(−)-ephedrine/LiAlH$_4$

Reduction of Imine III was performed in a manner similar to that of Example III using (1R,2S)-(−)-ephedrine as the chiral auxiliary. GC/EI-MS analysis showed about a 3% yield of (R)-(+)-N-(3-phenylpropyl)-1-(3-methoxyphenyl) ethylamine. The product was not analyzed by chiral HPLC. The results are reported in Table A.

Example VI

Reduction of Imine III with (1R,2S)-(−)-N-methylephedrine/LiAlH$_4$

Reduction of imine III was performed in a manner similar to that of Example III using (1R,2S)-(−)-N-methylephedrine as the chiral auxiliary. GC/EI-MS analysis showed a 64% yield of (R)-(+)-N-(3-phenylpropyl)-1-(3-methoxyphenyl) ethylamine. Preparative TLC and chiral HPLC analysis (as in Example II) showed an enantiomeric excess (R enantiomer) of 68%. The results are reported in Table A.

Example VII

Reduction of Imine III with (S)-(+)-1-(2-pyrrolidinylmethyl)pyrrolidine/LiAlH$_4$ Reduction of imine III was performed in a manner similar to that of Example III using (S)-(+)-1-(2-pyrrolidinylmethyl)pyrrolidine as the chiral auxiliary.

GC/EI-MS analysis showed a 47% yield of (R)-(+)-N-(3-phenylpropyl)-1-3-methoxyphenyl)ethylamine. Preparative TLC and chiral HPLC analysis (as in Example II) showed an enantiomeric excess (R enantiomer) of 1%. The results are reported in Table A.

Example VIII

Reduction of Imine III with (S)-(-)-1-methyl-2-pyrrolidine Methanol/LiAlH$_4$

Reduction of imine III was performed in a manner similar to that of EXAMPLE III using (S)-(-)-1-methyl-2-pyrrolidinemethanol as the chiral auxiliary. GC/EI-MS analysis showed a 67% yield of (R)-(+)-N-(3-phenylpropyl)-1-(3-methoxyphenyl)ethylamine. Preparative TLC and chiral HPLC analysis (as in Example II) showed an enantiomeric excess (S enantiomer) of 1%. The results are reported in Table A.

Example IX

Reduction of Imine III with (R)-(+)-α,α-diphenyl-2-pyrrolidine Methanol/LiAlH$_4$ Reduction of imine III was performed in a manner similar to that of Example III using (R)-(+)-α,α-diphenyl-2-pyrrolidinemethanol as the chiral auxiliary. GC/EI-MS analysis showed a 53% yield of (R)-(+)-N-(3-phenylpropyl)-1-(3-methoxyphenyl)ethylamine. Preparative TLC and chiral HPLC analysis (as in Example II) showed an enantiomeric excess (S enantiomer) of 1%. The results are reported in Table A.

Example X

Reduction of Imine III with (S)-(+)-2-(anilinomethyl)pyrrolidine/borane Complex

A 1M solution of borane-THF complex (about 1 ml [1 mmol]) was added to a cooled solution (about −78° C.) of diethyl ether (about 9 ml) and treated, dropwise, with a solution of (S)-(+)-2-(anilinomethyl)pyrrolidine (about 176 mg, 1 mmol) in diethyl ether. The reaction was stirred a room temperature for about 4 hours, cooled to about −78° C., and treated with a solution of the imine III (about 267 mg [1 mmol]) in diethyl ether (about 1 ml). The reaction was allowed to warm slowly to room temperature where it was stirred for about 72 hours. The reaction was quenched with 6N HCl, basified to a pH above about 12 with 10N NaOH and extracted with diethyl ether. GC/EI-MS analysis showed a 75% yield of (R)-(+)-N-(3-phenylpropyl)-1-(3-methoxyphenyl)ethylamine. Preparative TLC and chiral HPLC analysis (as in Example II) showed an enantiomeric excess (S enantiomer) of 7%. The results are reported in Table B.

Example XI

Reduction of Imine III with (S)-(-)-nicotine/BH$_3$

Reduction of imine III was performed in a manner similar to that of Example X using (S)-(-)-nicotine as the chiral auxiliary. GC/EI-MS analysis showed a 55% yield of (R)-(+)-N-(3-phenylpropyl)-1-(3-methoxyphenyl)ethylamine. Preparative TLC and chiral HPLC analysis (as in example II) showed an enantiomeric excess (S enantiomer) of 4%. The results are reported in Table B.

Example XII

Reduction of Imine III with (S)-(-)-1,1'-bi-2-naphthol/BH$_3$

Reduction of imine III was performed in a manner similar to that of Example X using (S)-(-)-1,1'-bi-2-naphthol as the chiral auxiliary. GC/EI-MS analysis showed a 2% yield of (R)-(+)-N-(3-phenylpropyl)-1-(3-methoxyphenyl)ethylamine. The product was not analyzed by chiral HPLC. The results are reported in Table B.

Example XIII

Reduction of Imine III with (1R,2S)-(-)-ephedrine/BH$_3$

Reduction of imine III was performed in a manner similar to that of Example X using (1R,2S)-(-)-ephedrine as the chiral auxiliary. GC/EI-MS analysis showed a 74% yield of (R)-(+)-N-(3-phenylpropyl)-1-(3-methoxyphenyl)ethylamine. Preparative TCL and chiral HPLC analysis (as in Example X) showed an enantiomeric excess (S enantiomer) of 1%. The results are reported in Table B.

Example XIV

Reduction of Imine III with (1R,2S)-(-)-N-methylephedrine/BH$_3$

Reduction of imine III was performed in a manner similar to that of Example X using (1R,2S)-(-)-N-methylephedrine as the chiral auxiliary. GC/EI-MS analysis showed a 45% yield of (R)-(+)-N-(3-phenylpropyl)-1-(3-methoxyphenyl)ethylamine. Preparative TLC and chiral HPLC analysis (as in Example X) showed no enantiomeric excess. The results are reported in Table B.

Example XV

Reduction of Imine III with (S)-(+)-1-(2-pyrrolidinyl methyl)pyrrolidine/BH$_3$

Reduction of imine III was performed in a manner similar to that of Example X using (S)-(+)-1-(2-pyrrolidinylmethyl)pyrrolidine as the chiral auxiliary. GC/EI-MS analysis showed a 54% yield of (R)-(+)-N-(3-phenylpropyl)-1-(3-methoxyphenyl)ethylamine. Preparative TLC and chiral HPLC analysis (as in Example X) showed an enantiomeric excess (R enantiomer) of 10%. The results are reported in Table B.

Example XVI

Reduction of Imine III with (S)-(-)-1-methyl-2-pyrrolidine Methanol/BH$_3$

Reduction of imine III was performed in a manner similar to that of Example X using (S)-(-)-1-methyl-2-pyrrolidine methanol as the chiral auxiliary. GC/EI-MS analysis showed a 60% yield of (R)-(+)-N-(3-phenylpropyl)-1-(3-methoxyphenyl)ethylamine. Preparative TLC and chiral HPLC analysis (as in Example X) showed no enantiomeric excess. The results are reported in Table B.

Example XVII

Reduction of Imine III with (R)-(+)-α,α-diphenyl-2-pyrrolidine Methanol/BH$_3$

Reduction of imine III was performed in a manner similar to that of Example X using (R)-(+)-α,α-diphenyl-2-pyrrolidinemethanol as the chiral auxiliary. GC/EI-MS analysis showed a 96% yield of (R)-(+)-N-(3-phenylpropyl)-1-(3-methoxyphenyl)ethylamine. Preparative TLC and chiral HPLC analysis (as in Example X) showed an enantiomeric excess (S enantiomer) of 5%. The results are reported in Table B.

Example XVIII

Preparation of 1-methyl-1-(3-methoxy)phenyl-5-(2-chloro)phenyl-2-aza-1-pentene (Imine V)

The imine V was prepared in a manner similar to that of imine III in Example I using 3-(2-chlorophenyl)propylamine and 3'-methoxyacetophenone. 3-(2-chlorophenyl) propylamine was obtained by the reduction ($BH_3$—$SMe_2$ complex) of 2-chlorohydrocinnamonitrile (Aldrich Chemical Co., Milwaukee, Wis., U.S.A.). This process afforded 1-methyl-1-(3-methoxy)phenyl-5-(2-chloro)phenyl-2-aza-1-pentene (imine V), a single component, as analyzed by GC/EI-MS: m/z (rel. int.) 301 ($M^+$, 1), 266 (22), 162 (100), 125 (26), 91 (13), 77 (9).

Example XIX

Reduction of Imine V with (R)-(+)-1,1'-bi-2-naphthol/$LiAlH_4$

Reduction of imine V was performed in a manner similar to that of Example III using (R)-(+)-1,1'-bi-2-naphthol as the chiral auxiliary. GC/EI-MS analysis showed a 15% yield of (R)-(+)-N-[3-(2-chlorophenyl)propyl]-1-(3-methoxyphenyl)ethylamine. Preparative TLC and chiral HPLC analysis (as in Example II) showed an enantiomeric excess (R enantiomer) of 12%. The results are reported in Table C.

Example XX

Reduction of Imine V with (S)-(−)-2-pyrrolidinemethanol/$LiAlH_4$

Reduction of imine V was performed in a manner similar to that of Example III, using (S)-(+)-2-pyrrolidinemethanol as the chiral auxiliary. No (R)-(+)-N-[3-(2-chlorophenyl)propyl]-1-(3-methoxyphenyl)ethylamine was detected from the reaction as analyzed by GC/EI-MS. The results are reported in Table C.

Example XXI

Reduction of Imine V with (1R,2S)-(−)-ephedrine/$LiAlH_4$

Reduction of imine V was performed in a manner similar to that of Example III using (1R,2S)-(−)-ephedrine as the chiral auxiliary. GC/EI-MS analysis showed a 3% yield of (R)-(+)-N-[3-(2-chlorophenyl)propyl]-1-(3-methoxyphenyl) ethylamine. Preparative TLC and chiral HPLC analysis (as in Example II) showed an enantiomeric excess (R enantiomer) of 40%. The results are reported in Table C.

Example XXII

Reduction of Imine V with (1R,2S)-(−)-N-methylephedrine/$LiAlH_4$

Reduction of imine V was performed in a manner similar to that of Example III using (1R,2S)-(−)-N-methylephedrine as the chiral auxiliary. GC/EI-MS showed a 31% yield of (R)-(+)-N-[3-(2-chlorophenyl)propyl]-1-(3-methoxyphenyl) ethylamine. Preparative TLC and chiral HPLC analysis (as in Example II) showed an enantiomeric excess (R enantiomer) of 41%. The results are reported in Table C.

Example XXIII

Reduction of Imine V with (1R,2S)-(−)-N-methylpsuedophedrine/$LiAlH_4$

Reduction of imine V was performed in a manner similar to that of Example III using (1R,2S)-(−)-N-methylpsuedophedrine as the chiral auxiliary. GC/EI-MS analysis showed a 28% yield of (R)-(+)-N-[3-(2-chlorophenyl)propyl]-1-(3-methoxyphenyl)ethylamine. Preparative TLC and chiral HPLC analysis (as in Example II) showed an enantiomeric excess (S enantiomer) of 31%. The results are reported in Table C.

Example XXIV

Reduction of Imine V with (2S,3R)-(+)-4-dimethylamino-1,2-diphenyl-3-methyl-2-butanol/$LiAlH_4$ Reduction of imine V was performed in a manner similar to that of Example III using (2S,3R)-(+)-4-dimethylamino-1,2-diphenyl-3-methyl-2-butanol as the chiral auxiliary. No (R)-(+)-N-[3-(2-chlorophenyl)propyl]-1-(3-methoxyphenyl)ethylamine was detected from the reaction as analyzed by GC/EI-MS. The results are reported in Table C.

Example XXV

Reduction of Imine V with (S)-(+)-1-(2-pyrrolidinylmethyl) Pyrrolidine/$LiAlH_4$ Reduction of imine V was performed in a manner similar to that of Example III using (S)-(+)-1-(2-pyrrolidinylmethyl)pyrrolidine as the chiral auxiliary. No (R)-(+)-N-[3-(2-chlorophenyl)propyl]1-(3-methoxyphenyl) ethylamine was detected from the reaction as analyzed by GC/EI-MS. The results are reported in Table C.

Example XXVI

Reduction of Imine V with (S)-(−)-α,α-diphenyl-2-pyrrolidine Ethanol/$LiAlH_4$

Reduction of imine V was performed in a manner similar to that of Example III using (S)-(−)-α,α-diphenyl-2-pyrrolidinemethanol as the chiral auxiliary. GC/EI-MS analysis showed a 6% yield of (R)-(+)-N-[3-(2-chlorophenyl)propyl]-1-(3-methoxyphenyl)ethylamine. Preparative TLC and chiral HPLC analysis (as in Example II) showed an enantiomeric excess (S enantiomer) of 8%. The results are reported in Table C.

Example XXVII

Reduction of Imine V with (S)-(+)-2-(anilinomethyl) Pyrrolidine/$LiAlH_4$

Reduction of imine V, was performed in a manner similar to that of Example III using (S)-(+)-2-(Anilinomethyl) pyrrolidine as the chiral auxiliary. No (R)-(+)-N-[3-(2-chlorophenyl)propyl]-1-(3-methoxyphenyl)ethylamine was detected from the reaction as analyzed by GC/EI-MS. The results are reported in Table C.

TABLE A

Chiral reduction[a] of imine III yielding (R)-(+)-N-(3-phenylpropyl)-1-(3-methoxyphenyl)ethylamine

| Example | Product[b] | ee %[c] |
|---|---|---|
| II | 100 | 17 (R) |
| III | 78 | 3 (S) |
| IV | 24 | 16 (S) |
| V | 3 | NA[d] |

TABLE A-continued

Chiral reduction[a] of imine III yielding
(R)-(+)-N-(3-phenylpropyl)-1-(3-methoxyphenyl)ethylamine

| Example | Product[b] | ee %[c] |
|---|---|---|
| VI | 64 | 68 (R) |
| VII | 47 | 1 (R) |
| VIII | 67 | 1 (S) |
| IX | 53 | 1 (S) |

[a]Lithium aluminum hydride-chiral auxiliary complex (see Examples II–IX).
[b]As analyzed by GC/EI-MS (Percentage yield).
[c]As analyzed by chiral HPLC.
[d]Not analyzed.
(S) indicates an enantiomeric excess ("ee") of the (S) enantiomer
(R) indicates an enantiomeric excess ("ee") of the (R) enantiomer

TABLE B

Chiral reduction[a] of imine III yielding
(R)-(+)-N-(3-phenylpropyl)-1-(3-methoxyphenyl)ethylamine

| Example | Product[b] | ee %[c] |
|---|---|---|
| X | 75 | 7 (S) |
| XI | 55 | 4 (S) |
| XII | 2 | NA[d] |
| XIII | 74 | 1 (S) |
| XIV | 45 | 0 |
| XV | 54 | 10 (R) |
| XVI | 60 | 0 |
| XVII | 96 | 5 (S) |

[a]Borane-chiral auxiliary complex (see Examples X-XVII).
[b]As analyzed by GC/EI-MS C percentage yield.
[c]As analyzed by chiral HPLC.
[d]Not analyzed.
(S) indicates an enantiomeric excess ("ee") of the (S) enantiomer
(R) indicates an enantiomeric excess ("ee") of the (R) enantiomer

TABLE C

Chiral reduction[a] of imine V yielding
(R)-(+)-N-[3-(2-chlorophenyl)propyl]-1-(3-methoxyphenyl)ethylamine

| Example | Product[b] | ee %[c] |
|---|---|---|
| XIX | 15 | 12 (R) |
| XX | 0 | NA[d] |
| XXI | 3 | 40 (R) |
| XXII | 31 | 41 (R) |
| XXIII | 28 | 31 (S) |
| XXIV | 0 | NA[d] |
| XXV | 0 | NA[d] |
| XXVI | 6 | 8 (S) |
| XXVII | 0 | NA[d] |

[a]Lithium aluminum hydride-chiral auxiliary complex (see Examples XVIII-XXVII).
[b]As analyzed by GC/EI-MS C percentage yield.
[c]As analyzed by chiral HPLC.
[d]Not analyzed.
(S) indicates an enantiomeric excess ("ee") of the (S) enantiomer
(R) indicates an enantiomeric excess ("ee") of the (R) enantiomer Although the invention has been described with the use of various examples and preferred embodiments, these are illustrative only, and the scope of the invention is to be determined by the appended claims.

What is claimed is:

1. A process for preparing an R enantiomer of a compound having a formula (I):

wherein Me is methyl, Ar is 3-methoxyphenyl, 3-chlorophenyl, or 1-naphthyl, and X is independently selected from the group consisting of H, F, Cl, Br, I, phenyl, $CF_3$, $CF_2H$, $CFH_2$, lower alkyl, O-lower alkyl, $OCH_2CF_3$, OH, CN, $NO_2$, C(O)-lower alkyl, C(O)O-lower alkyl, C(O)NH-lower alkyl, C(O)N-lower alkyl$_2$, OC(O)-lower alkyl, and NH—C(O)-lower alkyl, wherein m is an integer between 1 and 5, said process comprising:

asymmetrically and enantioselectively reducing an imine having a formula (II):

with a reducing agent selected from the group of borane and lithium aluminum hydride modified by a chiral auxiliary agent selected from the group consisting of (S)-(+)-2-(anilinomethyl)pyrrolidine, (1R,2S)-(−)-ephedrine, (1R,2S)-(−)-N-methylephedrine, (S)-(+)-1-(2-pyrrolidinylmethyl)pyrrolidine, (R)-(+)-1,1'-bi-2-naphthol, so as to produce an enantiomeric excess of the R enantiomer of the compound of formula (I) over the S enantiomer of the compound of formula (I).

2. The process according to claim 1 wherein said reducing agent is lithium aluminum hydride, and said chiral auxiliary agent is selected from the group consisting of (S)-(+)-2-(anilinomethyl)pyrrolidine, (1R,2S)-(−)-ephedrine, (1R,2S-(−)-N-methylephedrine and (R)-(+)-1,1'-bi-2-naphthol.

3. The process according to claim 1 wherein said reducing agent is lithium aluminum hydride, and said chiral auxiliary agent is selected from the group consisting of (S)-(+)-2-(anilinomethyl)pyrrolidine, (1R,2S)-(−)-ephedrine, (1R,2S),-(−)-N-methylephedrine, and (R)-(+)-1,1'-bi-2-naphthol.

4. The process according to claim 1 wherein said reducing agent is borane, and said chiral auxiliary is (S)-(+)-1-(2-pyrrolidinylmethyl)pyrrolidine.

5. The process according to claim 1 wherein the compound of formula (I) is (R)-(N)-[1-(3-methoxyphenyl)ethyl]-3-(2-chlorobenzene)propanamine](R)-(+)-(N)-[1-(3-methoxyphenyl)ethyl-3-(2-chlorobenzene)propanamine.

6. The process according to claim 1 wherein the compound of formula (I) is [(R)-(N)-[1-(3-methoxyphenyl)ethyl]-3-(2-chlorobenzene)propanamine](R)-(+)-N-[1-(3-methoxyphenyl)ethyl]-3-(phenyl)propanamine.

7. The process according to claim 5 wherein said reducing agent is lithium aluminum hydride, and said chiral auxiliary agent is (1R,2S)-(−)-N-methylephedrine.

8. The process according to claim 1 wherein the imine of the formula (II) is formed by the condensation of 3-(2-chlorophenyl)propylamine with 3'-methoxyacetophenone.

9. The process according to claim 1 where the compound of formula (I) is produced in an enantiomeric excess of the R enantiomer over the S enantiomer in an amount greater than 10%.

10. The process according to claim 1 where the compound of formula (I) is produced in an enantiomeric excess of the R enantiomer over the S enantiomer in an mount greater than 15%.

11. The process according to claim 1 where the compound of formula (I) is produced in an enantiomeric excess of the R enantiomer over the S enantiomer in an amount greater than 40%.

12. The process according to claim 1 where the compound of formula (I) is produced in an enantiomeric excess of the R enantiomer over the S enantiomer in an amount greater than 65%.

13. The process according to claim 1 wherein said chiral auxiliary agent is selected from the group consisting of (S)-(+)-2-(anilinomethyl)pyrrolidine, (1R,2S)-(−)-ephedrine, (1R,2S),-(−)-N-methylephedrine, and (R)-(+)-1,1'-bi-2-naphthol.

14. The process according to claim 1 wherein the reducing agent is lithium aluminum hydride and the chiral auxiliary agent is (S)-(+)-2-(anilinomethyl)pyrrolidine.

15. The process according to claim 1 wherein the reducing agent is lithium aluminum hydride and the chiral auxiliary agent is (R)-(+)-1,1'-bi-2-naphthol.

16. The process according to claim 1 wherein the reducing agent is lithium aluminum hydride and the chiral auxiliary agent is (1R,2S)-(−)-ephedrine.

17. A process for preparing an R enantiomer of a compound having a formula (I):

wherein Me is methyl, Ar is 3-methoxyphenyl, 3-chlorophenyl, or 1-naphthyl, and X is independently selected from the group consisting of H, F, Cl, Br, I, phenyl, $CF_3$, $CF_2H$, $CFH_2$, lower alkyl, O-lower alkyl, $OCH_2CF_3$, OH, CN, $NO_2$, C(O)-lower alkyl, C(O)O-lower alkyl, C(O)NH-lower alkyl, C(O)N-lower alkyl$_2$, OC(O)-lower alkyl, and NH—C(O)-lower alkyl, wherein m is an integer between 1 and 5, said process comprising:

asymmetrically and enantioselectively reducing an imine having a formula (II):

with borane modified by chiral auxiliary agent (S)-(+)-1-(2-pyrrolidinylmethyl)pyrrolidine, so as to produce an enantiomeric excess of R enantiomer of the compound of formula (I) over S enantiomer of the compound of formula (I).

18. A process for preparing an R enantiomer of (N)-[1-(3-methoxyphenyl)ethyl]-3-(2-chlorobenzene)propanamine, said process comprising:

asymmetrically and enantioselectively reducing 1-methyl-1-(3-methoxy)phenyl-5-phenyl-2-aza-1-pentene with lithium aluminum hydride modified by chiral auxiliary agent (1R,2S)-(−)-N-methylephedrine, so as to produce an enantiomeric excess of R enantiomer of (N)-[1-(3-methoxyphenyl)ethyl]-3-(2-chlorobenzene)propanamine over S enantiomer of (N)-[1-(3-methoxyphenyl)ethyl]-3-(2-chlorobenzene)propanamine.

19. The process according to claim 18 wherein the (N)-[1-(3-methoxyphenyl)ethyl]-3-(2-chlorobenzene)propanamine is produced in an enantiomeric excess of the R enantiomer over the S enantiomer in an amount greater than 15%.

20. The process according to claim 18 wherein the (N)-[1-(3-methoxyphenyl)ethyl]-3-(2-chlorobenzene)propanamine is produced in an enantiomeric excess of the R enantiomer over the S enantiomer in an amount greater than 40%.

* * * * *

UNITED STATES PATENT AND TRADEMARK OFFICE
CERTIFICATE OF CORRECTION

PATENT NO. : 5,648,541
DATED : July 15, 1997
INVENTOR(S) : VanWagenen et al.

It is certified that error appears in the above-identified patent and that said Letters Patent is hereby corrected as shown below:

On the Title Page in the second column, line 1, change "an" to --An--;

On the Title Page in the second column, line 23, change "Hydrognation" to --Hydrogenation--;

On the Title Page (page 2) in the first column, line 4, change "Acyloxyborogyrides" to --Acyloxyborohydrides--;

On the Title Page (page 2) in the first column, line 7, change "Ethanoloam" to --Ethanolam--;

In column 1, line 40, change "mines" to --amines--;

In column 1, line 49, change "et at." to --et al.--;

In column 9, line 64, change "methylpsuedophedrine" to --methylpsuedoephedrine--;

In column 10, line 1, change "methylpsuedophedrine" to --methylpsuedoephedrine--;

In column 10, line 36, change "Ethanol" to --methanol--;

In column 11, line 32, change "C percentage yield" to --(percentage yield)--;

In column 11, line 53, change "C percentage yield" to --(percentage yield)--;

In column 12, line 66, change "mount" to --amount--.

Signed and Sealed this

Twenty-seventh Day of October, 1998

Attest:

BRUCE LEHMAN

*Attesting Officer*          *Commissioner of Patents and Trademarks*